United States Patent [19]

Wojtech et al.

[11] Patent Number: 4,626,605

[45] Date of Patent: Dec. 2, 1986

[54] PROCESS FOR EXTRACTING PHENOLS FROM AQUEOUS SOLUTIONS

[75] Inventors: Bernhard Wojtech, Bad Soden am Taunus; Manfred Mayer, Niedernhausen; Karl-Erich Ott, Hamburg, all of Fed. Rep. of Germany

[73] Assignee: Hoechst Aktiengesellschaft, Frankfurt am Main, Fed. Rep. of Germany

[21] Appl. No.: 783,341

[22] Filed: Oct. 2, 1985

[30] Foreign Application Priority Data

Oct. 4, 1984 [DE] Fed. Rep. of Germany ....... 3436349

[51] Int. Cl.$^4$ ..................... C07C 37/82; C07C 37/70
[52] U.S. Cl. ................................... 568/757; 568/749
[58] Field of Search ............................... 568/757, 749

[56] References Cited

U.S. PATENT DOCUMENTS

| | | | |
|---|---|---|---|
| 2,113,951 | 4/1938 | Shuman | 568/757 |
| 2,812,305 | 11/1957 | Manka | 568/757 |
| 3,285,973 | 11/1966 | Arai et al. | 568/757 |

FOREIGN PATENT DOCUMENTS

| | | | |
|---|---|---|---|
| 535949 | 1/1957 | Canada | 568/757 |
| 0118523 | 7/1982 | Japan | 568/757 |
| 0165332 | 10/1982 | Japan | 568/757 |
| 2095253 | 9/1983 | United Kingdom | 568/757 |

OTHER PUBLICATIONS

Ullmann's Encyclopedia of Industrial Chemistry, 4th Edition, vol. 18, p. 186.

K. Haupke and F. Wolf, in Chem. Techn. 18, (1966), 405–410.

*Primary Examiner*—Werren B. Lone
*Attorney, Agent, or Firm*—Curtis, Morris & Safford

[57] ABSTRACT

The invention relates to a process for extracting phenols from aqueous solutions. The extractant used is a salt of an aliphatic amine, having a total carbon number of at least 10, and a strong acid.

7 Claims, No Drawings

PROCESS FOR EXTRACTING PHENOLS FROM AQUEOUS SOLUTIONS

The invention relates to a process for extracting phenols from aqueous solutions.

Such processes are already known. The phenol extraction from industrial effluents, such as are obtained in coal gasification, coal liquefaction, petroleum processing or in the manufacture of phenolic resins, is carried out on a large industrial scale. The oldest large-scale process, the benzene/caustic process, uses benzene as the extractant and then caustic soda for re-extracting the phenol from the benzene phase. Due to the low extraction capacity of benzene (the partition coefficient D=phenol concentration in the organic phase:phenol concentration in the aqueous phase is about 2.5:1) the outlay for the extraction (quantity of extractant, number of stages) is large. An improvement of the extraction is obtained by the Phenosolvan process (Lurgi) which uses diisopropyl ether as the extractant and reaches D-values of about 30:1. The further development led to even more active extractants, such as n-butyl acetate ($D \approx 71$) and methyl isobutyl ketone ($D \approx 82$). The state of the art is described in "Ullmanns Encyclopädie der technischen Chemie [Ullmann's Encyclopedia of Industrial Chemistry]", 4th Edition, Volume 18, page 186.

A prerequisite for all the extraction processes is the presence of an acidic effluent, because phenol is capable of forming hydrogen bonds only in its undissociated acidic form ($C_6H_5OH$) and thus becomes extractable.

In addition to the abovementioned conventional extractants, higher primary, secondary and tertiary amines, dissolved in aliphatic or aromatic hydrocarbons, are also suitable (K. Häupke and F. Wolf, in Chem. Techn. 18 (1966), 405–410). The advantage of higher amines over the conventional extractants is their insolubility in water, and their disadvantage is the markedly lower extraction effect.

It has now been found that the extraction capacity for phenols is increased 10 to 100-fold when, instead of the amines, their salts formed by association with mineral acids (ion pairs) are used as the extractant.

The invention relates to a process for extracting phenols from aqueous solutions, wherein the extractant used is a salt of an aliphatic amine, having a total carbon number of at least 10, and a strong acid. Preferably, a mineral acid is employed as the strong acid.

The amine salt is formed simply and quantitatively by mixing a strong acid with the amine, and in the case of mineral acids, the latter is transferred from the aqueous phase into the organic phase, ion pairs being formed. The equilibrium of this "neutralization" is entirely on the side of the amine salt. The equilibrium constants amount to $10^4$ to $10^8$, depending on the amine, the acid and, if present, the diluent. Such amine salts have the composition $(RH_2NH)X$, $(R_2HNH)X$ or $(R_3NH)X$, X being the anion of the acid, such as, for example, $Cl^-$, $SO_4^=$, $NO_3^-$, $ClO_4^-$ and $HPO_4^=$. The aliphatic amines can be primary, secondary or tertiary, and the alkyl radical or radicals have in total at least 10, preferably 20 to 50 carbon atoms and can be straight-chain, cyclic or branched. Amongst the said amines, the tertiary amines such as tri-n-octylamine, tri-isooctylamine, tri-n-decylamine, tri-isodecylamine, tri-n-dodecylamine, tri-isododecylamine or mixtures thereof are particularly preferred, because of their low chemical reactivity.

The amine salts can be introduced in an undiluted form, but they can also have been diluted with a solvent in order to reduce the viscosity. A partial conversion—at least 10%—of the amine into the amine salt is also possible, the remaining (free) amine acting as a diluent.

The acid for forming the amine salt can also be added to the aqueous phenol-containing phase which then, in contact with the amine, forms the extraction-active amine salt.

The phenol concentration in the aqueous phase can be as high as the saturation concentration. In addition to unsubstituted phenol ($C_6H_5OH$), alkylphenols or polyhydric phenols (for example resorcinol) and polyphenols (for example hydroxydiphenyls, dihydroxydiphenyls or dihydroxydiphenylmethanes) can also be extracted according to the invention. Of particular importance is the extraction of unsubstituted phenol, and also that of the cresols and xylenols, and of the other alkylphenols, the alkyl radical or radicals of which have a total of up to 5 carbon atoms.

The aqueous solutions of the phenols can also contain other dissolved organic or inorganic compounds and suspended particles, provided that these do not interfere with the extraction. A preceding extractive separation of interfering organic impurities is sometimes necessary. The extraction process according to the invention also allows the isolation of phenols from a high dilution, in particular from effluents, for example those having a phenol content of about 1% by weight or lower.

The extraction can be carried out, for example, continuously in counter-current in a multi-stage extractor, the extractant requirement relative to the aqueous phase being low, because of the high partition coefficients, so that the aqueous phase:organic phase ratio (phase ratio by volume) can be up to about 50:1.

An extensive concentration of the phenols in the extract is possible in this way. However, the high extraction capacity of the extractant also permits single-stage extraction in a stirred kettle, in which case the aqueous phase:organic phase ratio can be up to about 10:1.

In the case of the volatile phenols, such as $C_6H_5OH$, isolation of the phenols from the extract by distillation is possible. For this purpose, it is advantageous to use the amine salt without a volatile diluent. It is also advantageous to use the amine salt of a high-boiling amine, for example tri-n-octylamine (boiling point $\approx 350°$ C.) diluted with the free amine, i.e. to convert the amine only partially into the amine salt beforehand. The re-extraction of the phenols from the extract by treatment with caustic alkali, forming a phenolate, is likewise suitable.

The invention will be explained by reference to the examples which follow. In these, OP means organic phase and WP means aqueous phase.

EXAMPLE 1

A phenol-containing effluent from the manufacture of phenolic resins, containing 0.56 mmol/g of phenols, was extracted in counter-current in a mixer settler at room temperature with a solution of 1 mmol of amine sulfate per gram (prepared from 50:50 tri-n-octylamine and tri-n-decylamine) in a mixture of $C_{10}$–$C_{11}$-alkylbenzenes (commercially available under the name Solvesso ® 150) at an aqueous phase:organic phase ratio by volume of 1:1. The phenol concentration in the water phase fell, even in single-stage extraction, to a value of 0.03 mmol/g, corresponding to an extraction yield of 95%. Pure amine instead of amine sulfate at the same concentration in Solvesso 150 and under otherwise the same conditions gave a phenol concentration in the water phase of 0.046 mmol/g, corresponding to an extraction yield of 92%, only after 10 stages. The phenol was separated from the amine sulfate/Solvesso extract in a thin-layer evaporator at 90° C. in vacuo (0.1 mbar).

EXAMPLE 2

Samples of an aqueous solution of 5% by weight (0.531 mmol/g) of phenol were equilibrated in shaking vessels at room temperature and at various phase ratios by volume with an extractant which was composed, on the one hand, according to the invention of a solution of amine salts in Solvesso 150, and was then equilibrated for comparison with the free amine component in Solvesso 150 at the same molar amine concentration. The amine component employed was a mixture of tri-n-octylamine and tri-n-decylamine (50:50). The following amine salts were examined: amine sulfate $(R_3NH)_2SO_4$, amine chloride $(R_3NH)Cl$ and amine hydrogen phosphate $(R_3NH)_2HPO_4$. These salts were prepared in each case by mixing the amine dissolved in Solvesso 150 with an equivalent quantity of acid in aqueous solution, in shaking vessels under analytical control. The results are shown in Table 1.

TABLE 1

| No. | Phase ratio by volume WP:OP | Extract in Solvesso 150 | (mmol/g) | Phenol concentration (mmol/g) OP | WP | Partition coefficient |
|---|---|---|---|---|---|---|
| 1 | 2:1 | Amine | 0.5 | 0.824 | 0.155 | 5.3 |
| 2 | 2:1 | Amine hydrogen phosphate | 0.5 | 0.984 | 0.057 | 17.3 |
| 3 | 2:1 | Amine chloride | 0.5 | 0.972 | 0.060 | 16.2 |
| 4 | 2:1 | Amine sulfate | 0.5 | 1.028 | 0.037 | 27.8 |
| 5 | 1:1 | Amine | 0.5 | 0.489 | 0.094 | 5.2 |
| 6 | 1:1 | Amine hydrogen phosphate | 0.5 | 0.550 | 0.012 | 46 |
| 7 | 1:1 | Amine chloride | 0.5 | 0.563 | 0.010 | 56 |
| 8 | 1:1 | Amine sulfate | 0.5 | 0.570 | 0.0037 | 154 |
| 9 | 1:2 | Amine | 0.5 | 0.272 | 0.052 | 5.2 |
| 10 | 1:2 | Amine hydrogen phosphate | 0.5 | 0.291 | 0.0031 | 94 |
| 11 | 1:2 | Amine chloride | 0.5 | 0.293 | 0.0021 | 140 |
| 12 | 1:2 | Amine sulfate | 0.5 | 0.294 | 0.00059 | 498 |
| 13 | 2:1 | Amine | 1.0 | 0.907 | 0.112 | 8.1 |
| 14 | 2:1 | Amine sulfate | 1.0 | 1.103 | 0.0047 | 235 |
| 15 | 1:1 | Amine | 1.0 | 0.522 | 0.065 | 8.0 |
| 16 | 1:1 | Amine sulfate | 1.0 | 0.577 | 0.0014 | 412 |
| 17 | 1:2 | Amine | 1.0 | 0.284 | 0.035 | 8.1 |
| 18 | 1:2 | Amine sulfate | 1.0 | 0.294 | 0.00059 | 498 |

EXAMPLE 3

In single-stage partition tests with a phenol effluent from the manufacture of phenolic resin, the extraction capacity of a pure amine component (50:50 tri-n-octylamine and tri-n-decylamine) was compared with that of the same amine component which had been converted to the extent of 70 mol% into amine sulfates, under otherwise the same conditions at room temperature. The effluent had a concentration of phenols of 0.296 mmol/g. Table 2 shows the results.

TABLE 2

| No. | Phase ratio by volume WP:OP | Extractant A = pure amines B = 70 mol % of amine sulfate 30 mol % of amines | Phenol concentration (mmol/g) OP | WP | Partition coefficient |
|---|---|---|---|---|---|
| 1 | 1:1 | A | 0.300 | 0.0423 | 7.1 |
| 2 | 1:1 | B | 0.323 | 0.0072 | 44.9 |
| 3 | 2:1 | A | 0.565 | 0.0579 | 9.8 |

TABLE 2-continued

| No. | Phase ratio by volume WP:OP | Extractant A = pure amines B = 70 mol % of amine sulfate 30 mol % of amines | Phenol concentration (mmol/g) OP | WP | Partition coefficient |
|---|---|---|---|---|---|
| 4 | 2:1 | B | 0.639 | 0.0088 | 72.6 |
| 5 | 4:1 | A | 0.917 | 0.1013 | 9.1 |
| 6 | 4:1 | B | 1.234 | 0.0129 | 95.5 |

The substantially higher partition coefficients demonstrate the superior extraction capacity of the amine sulfate. Thus, for example, in experiment No. 4 with amine sulfate, an extraction yield of 97% was already reached in one stage, whereas only 80% were achievable with the free amine under the same conditions (experiment No. 3).

Even a 6-stage counter-current extraction at the same phase ratio by volume with the free amine gave an extraction yield of 93.6% only at a concentration of 0.02 mmol of phenol/g in the water phase. An extractor with theoretical stages was necessary for this, whereas the extraction with amine sulfate required only a stirred kettle.

EXAMPLE 4

100 ml of an aqueous solution were prepared which contained 5% by weight of phenol and 71 mmol of $H_2SO_4$ (=6.963 g). This is that quantity of sulfuric acid which is required for converting 100 ml of amine (50:50 tri-n-octylamine/tri-n-decylamine) to the extent of 70 mol% into the amine sulfate. The aqueous phenol solution containing sulfuric acid and 100 ml of the amine were then equilibrated at room temperature and the phenol content of the two phases was analyzed. In the organic phase, 0.526 mmol of phenol/g was found, and 0.00105 mmol of phenol/g was found in the aqueous phase, corresponding to a partition coefficient of 501/1. This extreme distribution coefficient shows that amine sulfate has been formed. The acid required for forming the amine sulfate can also be added to the aqueous phase, as shown by this example.

EXAMPLE 5

The following were introduced as the aqueous phases: an aqueous phenol solution of 0.531 mmol/g (5.0% by weight), an aqueous saturated p-cresol solution of 0.215 mmol/g (2.3% by weight) and an aqueous resorcinol solution of 0.443 mmol/g (4.9% by weight). The extraction capacity of the pure amine component (50:50 tri-n-octylamine/tri-n-decylamine) was compared with that of the same amine component which had been converted to the extent of 70 mol% into amine sulfate. Table 3 shows the results.

TABLE 3

| No. | Phase ratio by volume WP:OP | Extractant A = pure amines B = 70 mol % of amine sulfate, 30 mol % of amines | Extracted substance Name | Conc. in mmol/g OP | Conc. in mmol/g WP | Partition coefficient |
|---|---|---|---|---|---|---|
| 1 | 1:1 | A | Phenol | 0.569 | 0.512 | 11.1 |
| 2 | 1:1 | B | Phenol | 0.621 | 0.0015 | 414 |
| 3 | 2:1 | A | Phenol | 1.019 | 0.0889 | 11.5 |
| 4 | 2:1 | B | Phenol | 1.179 | 0.0034 | 347 |
| 5 | 4:1 | A | Phenol | 1.676 | 0.1418 | 11.8 |
| 6 | 4:1 | B | Phenol | 1.774 | 0.0177 | 100 |
| 7 | 1:1 | A | Resorcinol | 0.175 | 0.306 | 0.57 |
| 8 | 1:1 | B | Resorcinol | 0.492 | 0.0029 | 171 |
| 9 | 1:1 | A | Cresol | 0.226 | 0.012 | 19 |
| 10 | 1:1 | B | Cresol | 0.240 | 0.00064 | 375 |

We claim:

1. A process for reducing the phenol concentration of an aqueous solution, which comprises extracting the phenol from the aqueous solution with an extractant containing a salt of an aliphatic amine, having a total carbon number of at least 10, and a strong acid.

2. The process as claimed in claim 1, wherein the extractant contains a salt of a tertiary amine having a total carbon number of 20 to 50.

3. The process as claimed in claim 1, wherein the extractant contains an amine salt of hydrochloric acid, nitric acid, sulfuric acid or phosphoric acid.

4. The process as claimed in claim 1, wherein the amine salt is diluted in a solvent.

5. The process as claimed in claim 2, wherein the extractant contains an amine salt of hydrochloric acid, nitric acid, sulfuric acid or phosphoric acid.

6. The process as claimed in claim 2, wherein the amine salt is diluted in a solvent.

7. The process as claimed in claim 3, wherein the amine salt is diluted in a solvent.

* * * * *